United States Patent
Nagaoka et al.

(10) Patent No.: US 6,934,090 B2
(45) Date of Patent: Aug. 23, 2005

(54) VARIABLE OPTICAL ELEMENT, OPTICAL UNIT, AND IMAGE CAPTURING DEVICE

(75) Inventors: Toshiyuki Nagaoka, Tokyo (JP); Tetsuhide Takeyama, Tokyo (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 10/822,132

(22) Filed: Apr. 12, 2004

(65) Prior Publication Data

US 2004/0218283 A1 Nov. 4, 2004

(30) Foreign Application Priority Data

May 1, 2003 (JP) ........................................ 2003-126550

(51) Int. Cl.[7] .............................. G02B 9/00; G02B 7/02
(52) U.S. Cl. ...................................... 359/665; 359/819
(58) Field of Search ................................ 359/665–667, 359/819, 820, 620

(56) References Cited

U.S. PATENT DOCUMENTS

| | | | | |
|---|---|---|---|---|
| 5,071,229 A | * | 12/1991 | Oaki et al. | 417/540 |
| 5,150,234 A | * | 9/1992 | Takahashi et al. | 435/29 |
| 2002/0176148 A1 | | 11/2002 | Onuki et al. | 359/253 |
| 2004/0228003 A1 | * | 11/2004 | Takeyama et al. | 359/666 |

FOREIGN PATENT DOCUMENTS

| | | |
|---|---|---|
| JP | 2001-249203 | 9/2001 |
| JP | 2001-249261 | 9/2001 |

OTHER PUBLICATIONS

Claude Gabay et al.: *Dynamic study of a Varioptic variable focal lens*, Current Developments in Lens Design and Optical Engineering III, Proceedings of SPIE vol. 4767, 2002.

* cited by examiner

*Primary Examiner*—Ricky Mack
(74) *Attorney, Agent, or Firm*—Kenyon & Kenyon

(57) ABSTRACT

A variable optical element is formed by a first liquid member, a second liquid member which is unsoluble in the first liquid member, a container which contains the first liquid member and the second liquid member, an index for positioning the variable optical element according to a predetermined reference. In the variable optical element, an interfacial shape between the first liquid and the second liquid surface varies according to a voltage which is applied to the liquid members, and the index is disposed such that a wave front aberration in the variable optical element should be minimum or fewer than a predetermined value under condition that the variable optical element is positioned according to the predetermined reference. By doing this, it is possible to restrict the wave front aberration which is caused by a gravity in the variable optical element, the optical unit, and the image capturing device.

25 Claims, 10 Drawing Sheets

FIG.13A
FIG.13B
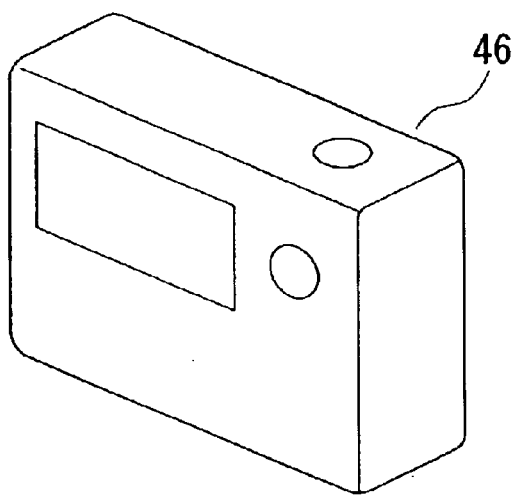
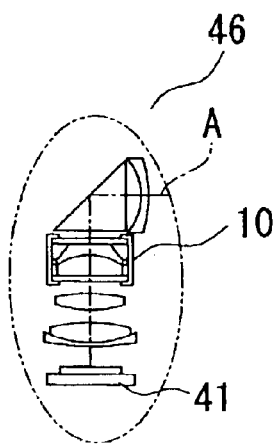
FIG.14
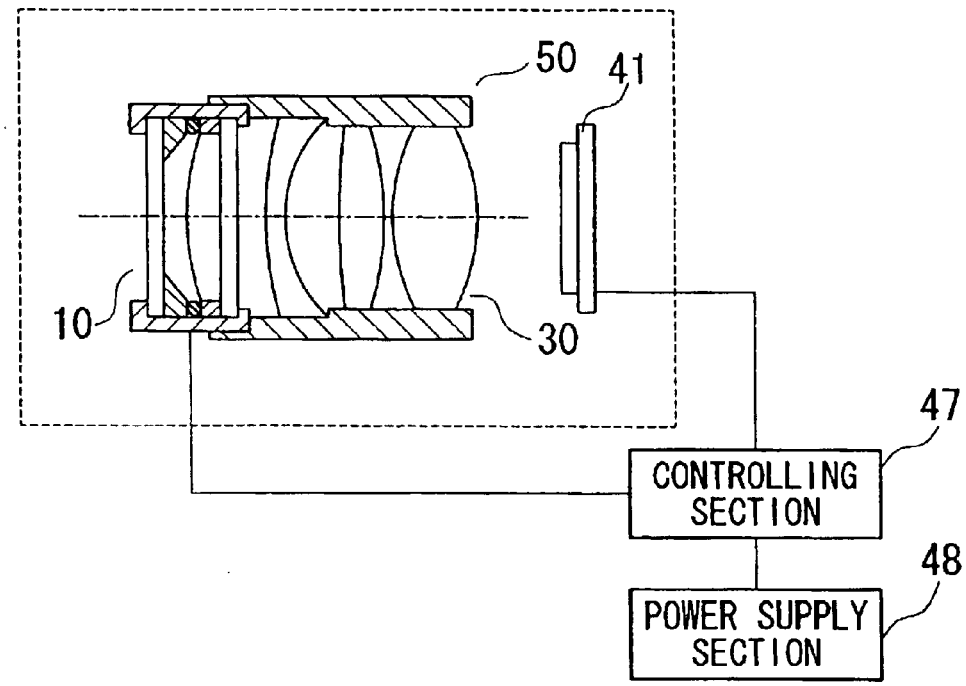

US 6,934,090 B2

VARIABLE OPTICAL ELEMENT, OPTICAL UNIT, AND IMAGE CAPTURING DEVICE

The present application is based on patent application No. 2003-126550 filed in May 1, 2003 Japan, the content of which is incorporated herein by reference.

BACKGROUND OF THE INVENTION

1. Field of the Invention

The present invention relates to a variable optical element, an optical unit, and an image capturing device.

2. Description of Related Art

In a conventional optical element of which focal distance is variable, it has been proposed that a first liquid member and a second liquid member which does not mix with the first liquid member are contained in a contained in an air-tight manner; thus, an interfacial shape varies such that the focal position may be variable (see Japanese Unexamined Patent Application, First Publication No. 2001-249261). In the optical element which is used in a device which is disclosed in the Japanese Unexamined Patent Application, First Publication No. 2001-249261, the first liquid member and the second liquid member having the same specific gravities as each other are contained in a container in an air-tight manner, and an electricity is applied to an electrode which is disposed on the container. By doing this, an interfacial tension between the first liquid member and the second liquid member varies. Therefore, in a lens which is formed by the second liquid member, a diameter, a thickness, and a curvature of a bottom surface of the lens vary. By doing this, the focal distance in the above optical element varies.

Also, as far as the above optical element is concerned, it is disclosed that an aberration occurs due to an influence of gravity. Here, it should be noted that such an aberration is generated under condition that there is a difference in a density between the two liquid members and that the optical element is disposed approximately parallel with the optical axis (see Japanese Unexamined Patent Application, First Publication No. 2001-249261, and "Current Developments in Lens Design and Optical Engineering III: PROCEEDING OF SPIE, VOL. 4767, 8–9, Jul. 2002").

SUMMARY OF THE INVENTION

A variable optical element of the present invention comprises a first liquid member, a second liquid member which is unsoluble in the first liquid member, a container which contains the first liquid member and the second liquid member, an index for positioning the variable optical element according to a predetermined reference. In this aspect of the present invention, it is preferable that an interfacial shape between the first liquid and the second liquid surface varies according to a voltage which is applied to the liquid members, and the index is disposed such that a wave front aberration in the variable optical element should be minimum or fewer than a predetermined value under condition that the variable optical element is positioned according to the predetermined reference.

An optical unit of the present invention comprises a variable optical element, and at least an optical element such that the index is disposed such that a wave front aberration in the variable optical element should be minimum or fewer than a predetermined value under condition that the variable optical element is positioned according to the predetermined reference.

An image capturing device of the present invention comprises a variable optical element, or an optical unit, and an image capturing element.

BRIEF DESCRIPTION OF THE DRAWINGS

FIG. 2A shows a condition under which there is not a wave front aberration. FIG. 2B shows a direction of the wave front aberration which is generated under condition a light is transmitted through a liquid member. FIG. 2C shows a direction of the wave front aberration which is caused under condition that a light is transmitted through a cover glass.

FIG. 4A shows other examples for positions of the mark. FIG. 4B shows other examples for shape of the mark.

FIG. 11A shows an entire structure of the mobile phone and FIG. 11B shows an optical system which is built in the mobile phone.

FIG. 12A shows an entire structure of the mobile terminal device. and FIG. 12B shows an optical system which is built in the mobile terminal device.

FIGS. 13A and 13B are examples in which the present invention is applied for a digital camera. FIG. 13A shows an entire structure of the digital camera and FIG. 13B shows an optical system which is built in the digital camera.

FIG. 14 is a view for showing a power supply for a variable optical element and an image capturing element.

DETAILED DESCRIPTION OF THE INVENTION

Figure 1:
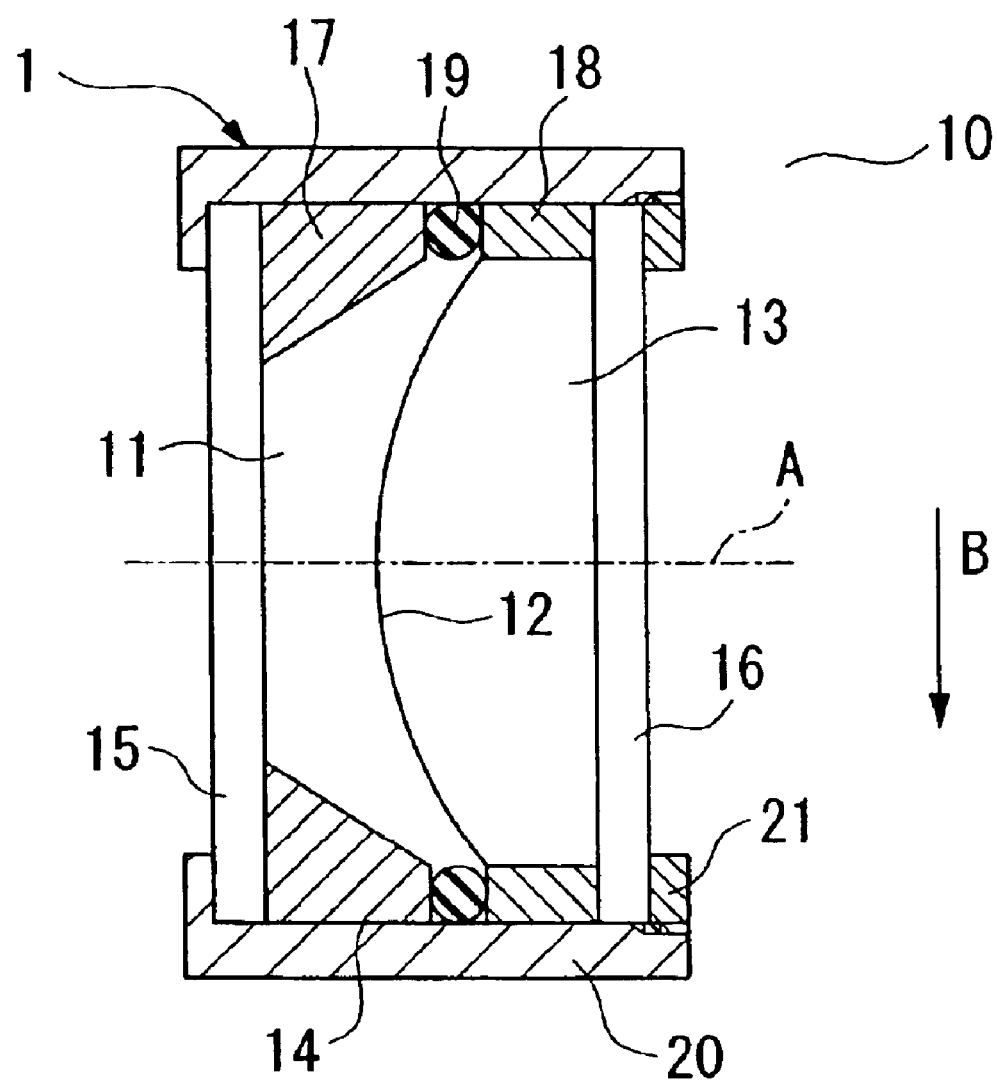
FIG. 1 is a cross section for a variable optical element according to a first embodiment of the present invention.

Aforesaid, a variable optical element comprises a first liquid member, a second liquid member which is unsoluble in the first liquid member, a container which contains the first liquid member and the second liquid member, an index for positioning the variable optical element according to a predetermined reference. In this aspect of the present invention, it is preferable that an interfacial shape between the first liquid and the second liquid surface varies according to a voltage which is applied to the liquid members, and the index is disposed such that a wave front aberration in the variable optical element should be minimum or fewer than a predetermined value under condition that the variable optical element is positioned according to the predetermined reference.

It is preferable that the predetermined reference is disposed horizontally, and an optical axis of the variable optical element is disposed so as to be parallel with the horizontal direction of the predetermined reference.

It is preferable that the variable optical element and the optical element.

It is preferable that a variable optical element further comprises a frame member for supporting the container wherein the index is disposed on the frame member.

It is preferable that shape of the frame member for supporting the container is rotationally asymmetrical around the optical axis.

It is preferable that the variable optical element is positioned according to the wave front aberration by measuring the surface of a transmitted wave.

It is preferable that a refractive index in the first liquid is different from a refractive index in the second liquid member.

An optical unit comprises a variable optical element, and at least an optical element. In this aspect of the present invention, it is preferable that the index is disposed such that a wave front aberration in the variable optical element should be minimum or fewer than a predetermined value under condition that the variable optical element is positioned according to the predetermined reference.

It is preferable that the predetermined reference is disposed horizontally, and an optical axis of the variable optical element is disposed so as to be parallel with the horizontal direction of the predetermined reference.

It is preferable that an optical unit having an optical system which comprises a variable optical element of which optical characteristics varies according to an interfacial shape between the first liquid and the second liquid according to a voltage which is applied to the liquid members, and at least a second optical element. In this aspect of the present invention, it is preferable that the variable optical element and the second optical element can make a relative rotation around the optical axis, the index is formed by a fist index which is disposed on the variable optical element and a second index which is disposed on the second optical element, and the first index and the second index indicate a relative angle position made by the variable optical element around the optical axis which is used horizontally and the optical axis.

It is preferable that the second optical element is a reflecting member.

It is preferable that the variable optical element is disposed so as to be near the optical axis which is returned by the reflecting member.

It is preferable that a central axis of the variable optical element is disposed so as to be approximately vertically parallel.

It is preferable that the reflecting member is a mirror.

It is preferable that the reflecting member is a prism.

It is preferable that an optical unit comprises a variable optical element, at least a second optical element, and two frame members for supporting the variable optical element and the second optical element. In this aspect of the present invention, it is preferable that the indices are disposed in the frame members respectively.

It is preferable that an optical unit comprises a variable optical element, and an optical system which is provided with a first group having a negative refracting force and a second group having a positive refracting force.

It is preferable that the optical system is disposed nearer the variable optical element than an object to be observed.

It is preferable that an image capturing device comprises a variable optical element or an optical unit; and an image capturing element.

It is preferable that an image capturing device further comprises a driving unit for driving the variable optical element, and a power supply unit for supplying an electricity to the image capturing element and the driving unit.

It is preferable that a mobile phone comprises a variable optical element, a displaying section, an inputting button section, a voice inputting-outputting section, and an antenna.

It is preferable that a digital camera comprises a variable optical element, a displaying section, and an operating section.

It is preferable that an endoscope device comprises a variable optical element, a light source, a signal processing circuit, and a power supply section.

It is preferable that a mobile terminal comprises a variable optical element, a displaying section, and a key board.

Hereinafter, a variable optical element according to a first embodiment is explained with reference to drawings below.

As shown in FIG. 1, a variable optical element 10 comprises a first liquid member 11, a second liquid member 13, and a container which contains the above liquid members thereinside. Here, the first liquid member 11 and the second liquid member 13 do not mix with each other such that an interface 12 is formed therebetween. That is, there is a tendency that both the first liquid member 11 and the second liquid member 13 are separated from each other by the interface 12 in an air-tight sealed space.

The container 14 comprises two cover glasses 15, 16, a first ring electrode 17, a second ring electrode 18, a ring seal member 19, and a frame member 20.

The cover glasses 15, 16 are formed by parallel plates. The both cover glasses 15, 16 are disposed so as to have a predetermined interval such that both plates should be parallel to each other. The first ring electrode 17, the ring seal member 19, and the second ring electrode 18 are disposed between the cover glasses 15, 16.

An outer surface of the first ring electrode 17 is cylindrical. An inner surface of the first ring electrode 17 is conical. An end surface of the first ring electrode 17 is disposed so as to contact the cover glass 15. The other end surface of the first ring electrode 17 is disposed so as to contact the ring seal member 19. The ring seal member 19 is an insulating member.

The second ring electrode 18 is disposed so as to be opposite to the first ring electrode 17 such that the ring seal member 19 is disposed therebetween. An outer surface and an inner surface of the second ring electrode 18 are cylindrical. An end surface of the second ring electrode 18 contacts the ring seal member 19. Also, the other end surface of the second ring electrode 18 contacts the cover glass 16.

Here, two cover glasses 15, 16, the electrodes 17, 18, and the ring seal member 19 have the common outer diameters.

Also, an outer surface and an inner surface of the frame member 20 are cylindrical. A protruding section is formed on an end surface of the frame member 20. An inner diameter of the frame member 20 is approximately the same as the outer diameter of the above members such as two cover glasses 15, 16, the electrodes 17, 18, and the ring seal member 19. Therefore, it is possible to insert the above members into the inner surface of the frame member 20.

In such a case, the cover glass 15 contacts the protruding section in the frame member 20. By doing this, positions of the above members are determined in the frame member 20. Furthermore, a screw section is formed on the inner surface of the frame member 20 opposite to the protruding section. On the other hand, a screw section is formed on an outer surface of a push ring 21. The outer diameter of the screw section is the same as the inner diameter of the screw section on the frame member 20. Therefore, it is possible to push the above members by the push ring 21 from the cover glass 16.

The first ring electrode 17 is disposed so as to contact the first liquid member 11. Also, the second ring electrode 18 is disposed so as to contact the second liquid member 13. It is possible to apply an electricity to the first ring electrode 17 and the second ring electrode 18 separately.

Figure 3:
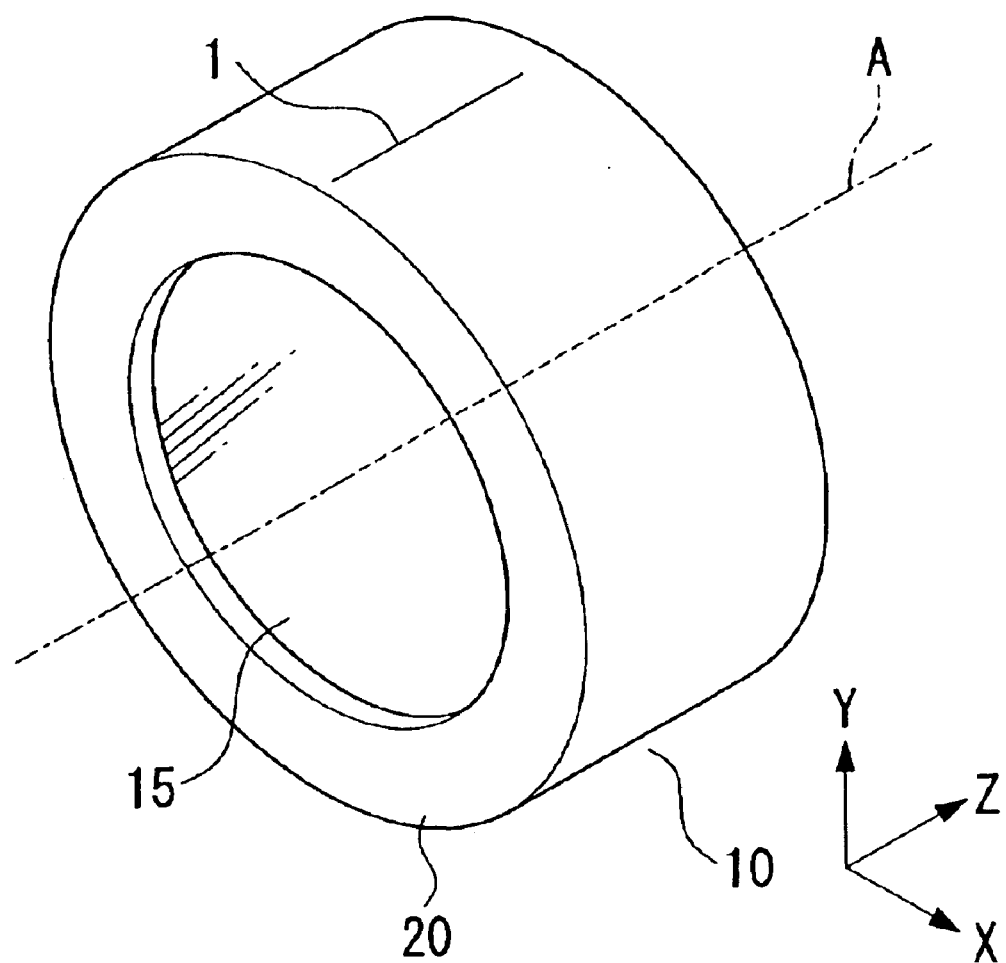
FIG. 3 is an isometric view for showing a position of a mark which is added to the variable optical element shown in FIGS. 2A to 2C.

Also, as shown in FIGS. 1 and 3, a mark (index) 1 is notched on the outer surface of the frame member 20. The mark 1 is added as follows. An arrow B indicates a vertical direction (gravity direction). A horizontal direction crosses the vertical direction orthogonally.

As shown in FIG. 1, a variable optical element 10 is disposed such that the optical axis should be horizontal. In such a case, the interface 12 is deformed by an influence of gravity. That is, the shape of the interface 12 is rotatively asymmetric around the optical axis A. Therefore, a wave front aberration is generated for a light which transmits through the variable optical element 10.

In the above structure, there is not a relationship in which the frame member 20 and the first liquid member 11 cooperate unitarily. The frame member 20 and the second liquid member 13 have the similar relationship with the above case. If the variable optical element 10 is rotated around the optical axis A, the frame member 20 rotates. However, the first liquid member 11 and the second liquid member 13 do not rotate. Therefore, the direction of the wave front aberration which is caused when the light transmits through these liquid members do not vary according to the rotation of the frame member 20.

Figure 2A:
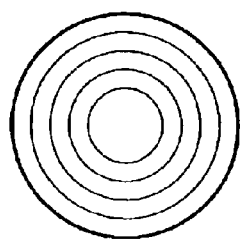
FIGS. 2A to 2C are view for showing directions of wave front aberrations under condition that the variable optical element is rotated around the optical axis.
Figure 2B:
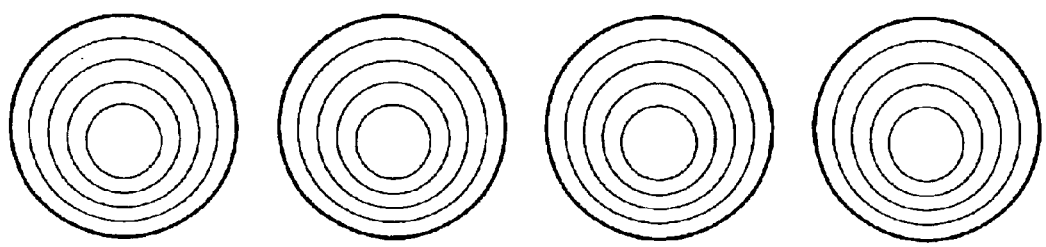
Figure 2C:
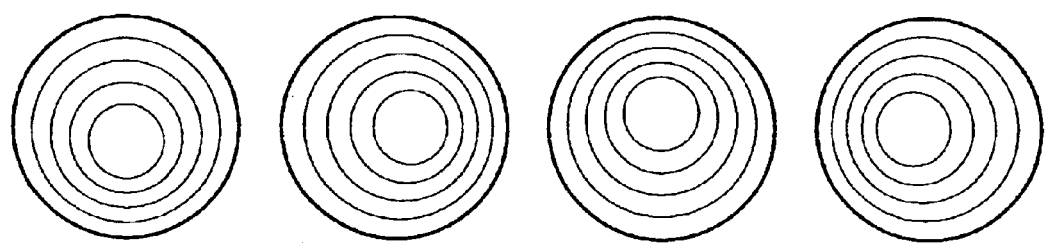

FIGS. 2A to 2C show the above conditions. FIG. 2A shows a condition under which there is not a wave front aberration. Here, a condition is shown under which a wave front (spherical wave) which is converted to a convergent light by the variable optical element 10 interferes with a plane wave. Centers of each circle are concentric under condition that there is not a wave front aberration. Therefore, intervals between interference fringes are equal. On the other hand, in FIG. 2B, a condition is shown under which there is a wave front aberration when a light transmits through the liquid members. In such a case, the center of each circle is shifted downward. As a result, intervals between interference fringes are not equal. Here, in FIG. 2B, the shifting direction of the circle is always downward even if the variable optical element 10 rotates. That is, the direction of the wave front aberration does not vary.

On the other hand, there is a case in which a wave front aberration is generated in the cover glasses 15, 16 due to a variance of manufacturing tolerance. Therefore, in such a case, the front aberration is generated for a light which transmits through the cover glasses 15, 16. Here, θ indicates a random angle for an initial position in a rotating direction.

In the above structure, the cover glasses 15, 16 are fixed on the frame member 20. Here, if the variable optical element 10 is rotated around the optical axis A, the cover glasses 15, 16 rotate according to the rotation of the frame member 20. Therefore, the direction of the wave front aberration which is generated when a light is transmitted through the cover glasses 15, 16 varies according to the rotation of the frame member 20. FIG. 2C shows a wave front aberration which is generated when a light is transmitted through the cover glasses. In FIG. 2C, it is understood that directions for shifting the center of circles are different. As shown in this drawing, it is understood that if the cover glasses 15, 16 rotate, the directions for shifting the center of circles varies. That is, the direction of the wave front aberration varies.

As explained above, if the variable optical element 10 is rotated around the optical axis A, the direction of the wave front aberration which is generated in the variable optical element 10 varies according to a rotational position around the optical axis A. Here, a position of the variable optical element 10 which is rotated by a predetermined angle is indicated by a rotational position.

As explained above, the wave front aberration which is generated in the variable optical element 10 is an accumulation of the wave front aberration which is generated due to the deformation of the interface 12 and the wave front aberration which is generated in the cover glasses 15, 16. In addition, the interface 12 which generates the wave front aberration and the cover glasses 15, 16 move differently according to the rotation. Thus, the variable optical element 10 is formed below by putting a focus on such a feature.

First, the variable optical element 10 is disposed appropriately such that the optical axis A of the variable optical element 10 should be horizontal. It is understood that such a position of the variable optical element 10 be an initial position. Next, an electricity is applied to the first ring electrode 17 and the second ring electrode 18 such that the interface 12 have a predetermined curvature. Consequently, a parallel light is incident into the variable optical element 10. By doing this, the light which is transmitted through the variable optical element 10 is condensed onto a focal position which is determined by the curvature of the interface 12. The wave front of the transmitted light is measured under such a condition. By doing this, the wave front aberration in the initial position is determined.

Next, the variable optical element 10 is rotated around the optical axis A by the predetermined angle. Consequently, the wave front aberration is measured under such a condition. After that, such rotations and the measurements for the wave front aberration are repeated by varying the rotational position until the rotational position returns to the initial position.

By doing this, when the variable optical element 10 returns to the initial position after rotating by 360°, every wave front aberrations at each rotational position are measured. According to such measurement results, it is possible to determine the rotational position in which the wave front aberration may be minimum.

Next, the variable optical element 10 which is disposed in such a rotational position is viewed from a reference position. Here, in the present embodiment, such a reference position is determined by viewing the cover glass 15 frontally (in a direction of optical axis A). The mark 1 is disposed in a highest position in the frame 20 with reference to the reference position.

Here, there are various standards for determining the mark 1. For example, it is possible to establish a virtual plane (Y-Z plane) which includes the optical axis A and a line which is orthogonal to the optical axis A. If such a virtual plane is established as a reference plane, it is understood that the mark 1 is disposed in the reference plane. Alternatively, it is possible to establish a virtual plane (X-Z plane) which includes the optical axis A and a horizontal line which is orthogonal to the optical axis A. If such a virtual plane is established as a reference plane, it is understood that the mark 1 is disposed in a position which is shifted by 90° counter-clock-wise from the reference plane the reference plane.

It is explained below how the mark 1 serves in the variable optical element 10 having the above structure.

For example, it is assumed that an image for an object is formed by the variable optical element 10. Also, it is assumed that the object is positioned horizontally far away. In such a case, the variable optical element 10 is disposed such that the optical axis A of the variable optical element 10 should be horizontal. In such a case, the variable optical element 10 is disposed such that the mark 1 should be disposed so as to coincide the highest position in the frame member 20 with reference to the reference position. Alternatively, after the variable optical element 10 is disposed appropriately, the variable optical element 10 is rotated around the optical axis A until the mark 1 is disposed at the highest position in the frame member 20. Here, the reference position is the same as a case in which the mark 1 is disposed. That is, such a reference position is indicated at a highest position on the frame member 20 under condition that the cover glass 15 is viewed frontally from the direction of the optical axis A for disposing the variable optical element 10.

By disposing the variable optical element 10 in the above manner, it is possible to restrict the wave front aberration which is generated in the variable optical element 10 in a minimum level.

Here, in the present embodiment, the explanation is made for a case in which the mark 1 is disposed in a part of the frame member 20. However, more importantly, the present embodiment is not limited to such a condition. For example, it is acceptable if the mark 1 is added by applying a part of a sealing member or by using a writing member such as a pen and a pencil. Also, it is acceptable if the mark 1 is disposed on a light-incident plane or a light-emitting plane as shown in FIG. 4A.

Also, it is acceptable if the mark 1 is disposed at any position such as a lowest position on the frame member 20. Also, it is acceptable if the mark 1 is disposed on a right most position or a left most position which is on the frame member 20 such that a horizontal line which connects the right most position and the left most position is orthogonal to a vertical diameter which is formed pass the optical axis A between the highest position and the lowest position on the frame member 20. In FIG. 3, the mark 1 is shown in the highest position on the frame member 20. However, more importantly, the position of the mark 1 is not limited to the above cases as long as it is possible to determine a certain rotational position around the optical axis A under condition that the optical axis A is disposed horizontally. In other words, it is possible to dispose the mark 1 at the lowest position on the frame member 20. In such a case, it is possible to dispose the variable optical element 10 such that the mark 1 is disposed at the lowest position on the frame member 20 when the variable optical element 10 is under operation.

Figure 4A:
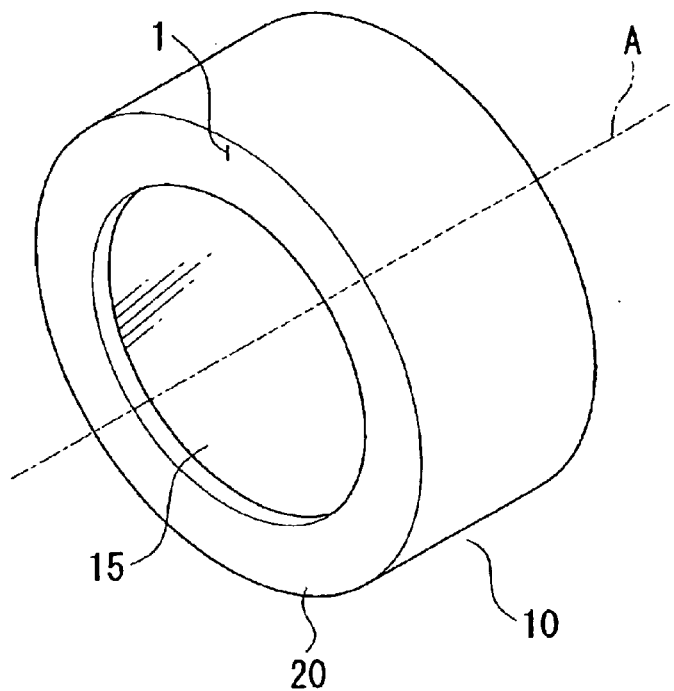
FIGS. 4A and 4B are examples for the marks which are added to the variable optical element which is shown in FIG. 3.
Figure 4B:
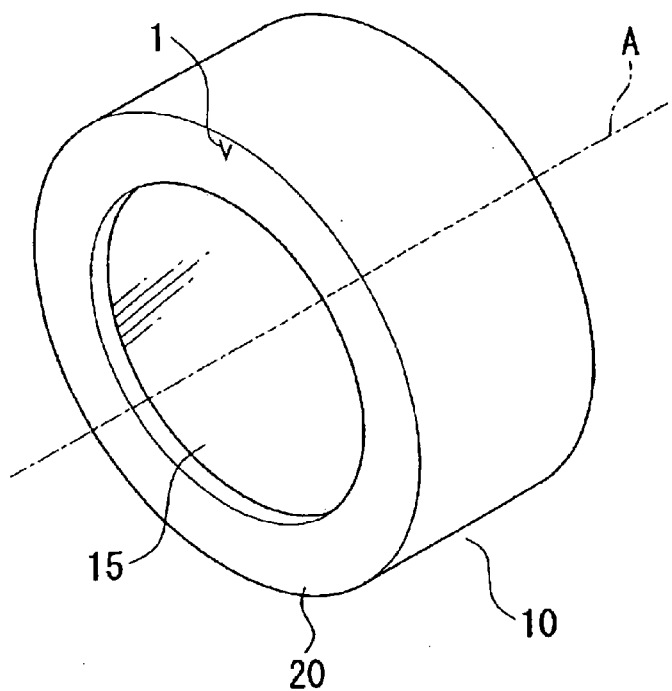

Here, it is possible to employ any form such as a "V-shape" shown in FIG. 4B for the mark 1 instead of a line shown in FIG. 4A. Also, it is preferable to dispose the mark 1 such that the mark 1 should not block a light flux which transmits through the variable optical element 10.

Also, in the present embodiment, the mark 1 is disposed at a rotational position such that the wave front aberration should be minimum. However, more importantly, it is not necessary to determine such a minimum value for the wave front aberration so exactly. Thus, it is acceptable the mark 1 is disposed such that the wave front aberration is fewer than a predetermined value.

Also, it is acceptable if the variable optical element 10 is rotated continuously for measuring the wave front aberration at each rotational position. Also, it is acceptable if the measurement for the wave front aberration is performed continuously. By doing this, it is possible to obtain a position for disposing the mark 1 more exactly.

Figure 5:
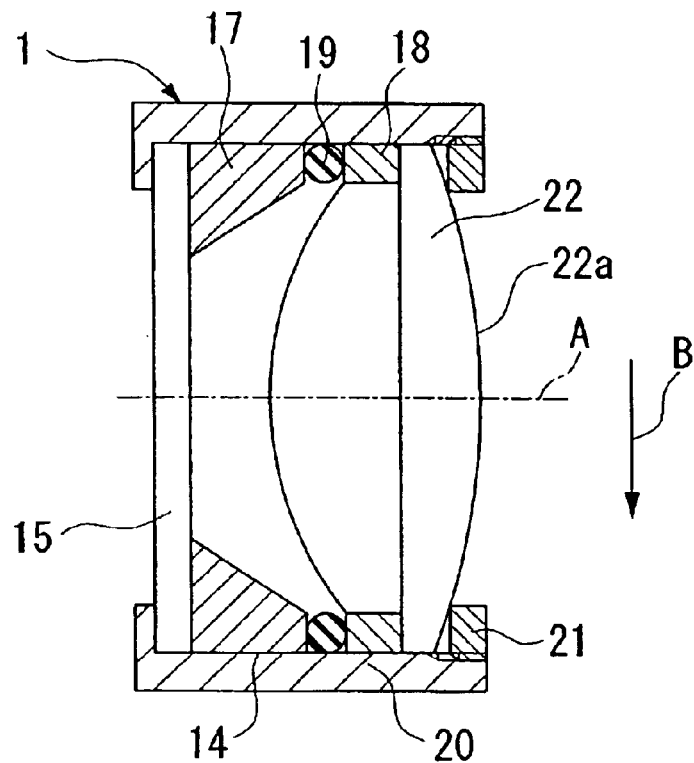
FIG. 5 is a modified example for the variable optical element shown in FIG. 2.

Also, as shown in FIG. 5, it is possible to employ a lens 22 which has a power instead of at least the cover glass 15 or 16 which is disposed at a light-incident end or a light-emitting end. Also, it is possible to form a surface 22a of the lens 22 by various surfaces such as a spherical surface, an aspherical surface, a refractive optical surface, and a free-form surface. Also, it is possible to use a glass member or a plastic member for the lens 22.

Figure 6:
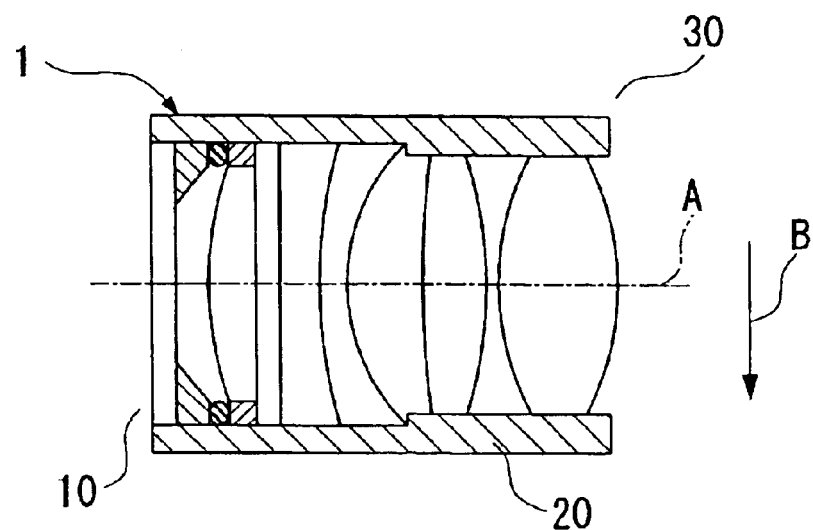
FIG. 6 shows examples for optical unit which use the variable optical elements shown in FIGS. 2A to 2C.

Also, as shown in FIG. 6, it is acceptable an optical unit 30 is formed by extending the frame member 20 and fixing a second optical element which is different from the variable optical element 10 unitarily. Consequently, it is acceptable if the optical unit 30 is rotated so as to dispose the mark 1 at a rotational position such that the entire wave front aberration should be minimum or less than a predetermined value.

Next, an image capturing device 40 according to a second embodiment is explained with reference to FIG. 7. Here, it should be noted that, in explanations for the image capturing device 40, the same reference numerals are applied to corresponding members as shown in the above explanation for the variable optical element 10 so as to omit the repeated explanation thereof.

Figure 7:
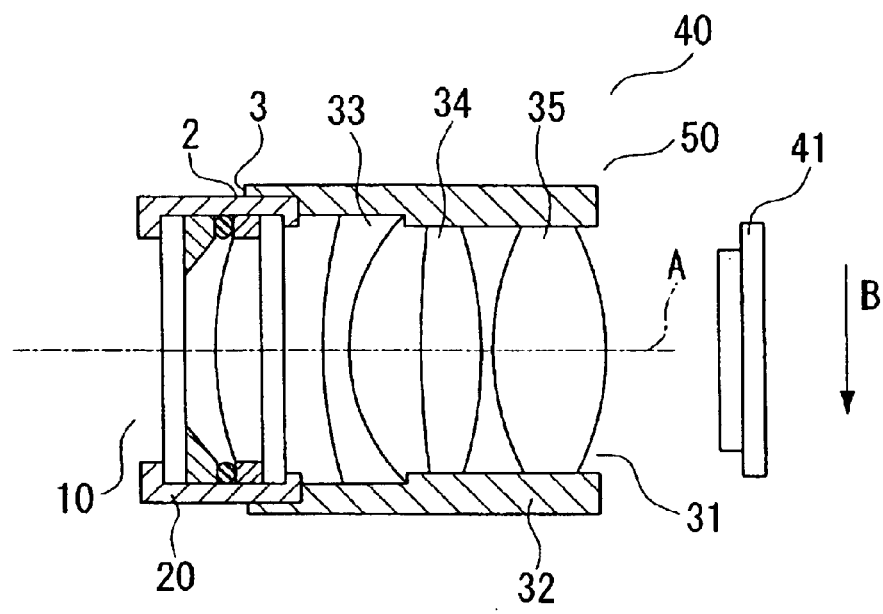
FIG. 7 is a cross section for an image capturing device according to a second embodiment of the present invention.

As shown in FIG. 7, the image capturing device 40 according to the present embodiment comprises an optical unit 50 for condensing a light and an image capturing element 41. The image capturing element 41 is disposed near a focal position in the optical unit 50.

The variable optical element 10 and an optical system 31 are supported by separated frame members 20 and 32 in the optical unit 50. The frame members 20 and 32 can be fitted to each other such that the optical axis A in the frame member 20 and the optical axis A in the frame member 32 coincide.

The optical system 31 comprises a concave lens 33, a convex lenses 34 and 35. These lenses serves as a separate optical elements from the variable optical element 10.

The image capturing element 41 is a charge coupled device (hereinafter called a CCD). The image capturing element 41 is disposed at a position of an image which is formed by the optical unit 50.

Figure 8:
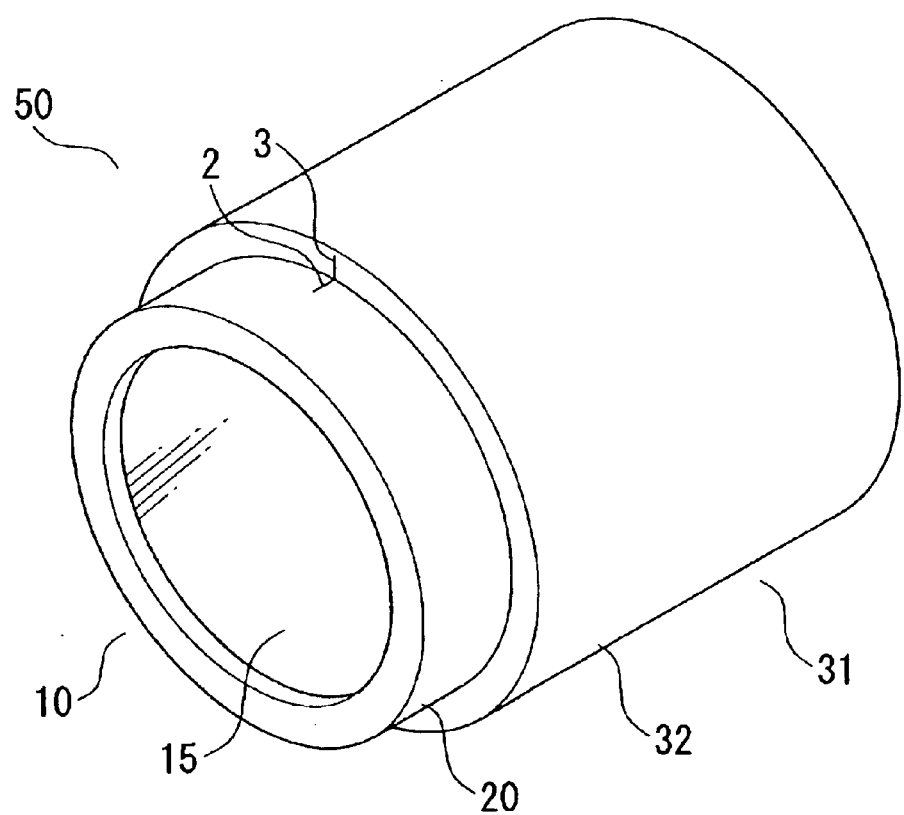
FIG. 8 is an isometric view for a position of a mark which is added to the variable optical element shown in FIG. 7.

Also, as shown in FIG. 8, for example, marks (indices) 2 and 3 are added on the optical unit 50 by a stamping operation. The mark 2 is disposed on an outer surface of the frame member 20. Also, the mark 3 is disposed on a light-incident end surface on the frame member 32.

These marks 2 and 3 are disposed as follows.

A first method for disposing the marks 2 and 3 is explained as follows. First, the variable optical element 10 is disposed such that the optical axis A should be horizontal. Consequently, as explained in the first embodiment, a position by which the wave front aberration should be minimum is obtained only by the variable optical element 10. After that, the mark 2 is disposed on the frame member 20 under condition that the variable optical element 10 is maintained in such a rotational position.

Next, the optical system 31 is fitted to the variable optical element 10. After that, the optical system 31 is rotated around the optical axis A while the variable optical element 10 is fixed. In such a case, the wave front aberration for an entire optical unit 50 is measured in each rotational position. The rotational position by which the wave front aberration should be minimum is obtained from the above measurement result. Consequently, the optical system 31 is rotated so as to coincide the rotational position of the optical system 31 should be at above rotational position. Finally, the frame member 20 and the frame member 32 are fixed at such a rotational position by a bonding agent.

Here, in a case in which the frame member 20 and the frame member 32 are not fixed together, a mark 3 is disposed on such a rotational position on the frame 32 such that a part of the mark 3 is connected to a part of the mark 2. This is for a purpose of convenience so as to dispose the variable optical element 10 and the optical system 31 separately.

Such a first method for disposing the marks 2 and 3 is effective in a case in which the wave front aberration which is generated in the optical system 31 is fewer than the wave front aberration which is generated in the cover glasses 15 and 16, and the interface 12.

A second method for disposing the marks 2 and 3 is explained as follows. First, the optical unit 50 is disposed appropriately. Next, the optical system 31 is fixed. Consequently, only the variable optical element 10 is rotated around the optical axis A. In such a case, the wave front aberration for the entire optical unit 50 is measured in each rotational position while rotating the variable optical element 10. Thus, a rotational position by which the wave front aberration for the entire optical unit 50 should be minimum can be obtained.

Under the above condition, the frame member 20 and the frame member 32 are fixed. Consequently, the entire optical unit 50 is rotated. In such a case, the wave front aberration for the entire optical unit 50 is measured at each rotational position. The rotational position by which the wave front aberration should be minimum is obtained from the above measurement result. Consequently, the optical unit 50 is rotated so as to coincide the rotational position of the optical unit 50 should be at above rotational position. After that, the mark 2 is disposed on the frame member 20. Alternatively, the mark 3 is disposed on the frame member 32.

Here, in a case in which the frame member 20 and the frame member 32 are not fixed together, a mark 3 is disposed on such a rotational position on the frame 32 such that a part of the mark 3 is connected to a part of the mark 2. This is for a purpose of convenience so as to dispose the variable optical element 10 and the optical system 31 separately.

Such a second method for disposing the marks 2 and 3 is effective in a case in which the wave front aberration which is generated in the interface 12 is fewer than the wave front aberration which is generated in the cover glasses 15 and 16, and the optical system 31. Here, in the above explanation, the variable optical element 10 is rotated while the optical system 31 is fixed. However, more importantly, it is acceptable if the optical system 31 is rotated while the variable optical element 11 is fixed.

A third method for disposing the marks 2 and 3 is explained as follows. First, the optical unit 50 is disposed appropriately. Next, the variable optical element 10 is fixed. Consequently, only the optical system 31 is rotated around the optical axis A. In such a case, the wave front aberration for the entire optical unit 50 is measured in each rotational position while rotating the optical system 31. Thus, a rotational position by which the wave front aberration for the entire optical unit 50 should be minimum can be obtained. After that, the mark 3 is disposed on the frame member 32 at a rotational position at which the wave front aberration should be minimum.

Consequently, the variable optical element 10 is rotated around the optical axis A. In such a case, the wave front aberration for the entire optical unit 50 is measured at each rotational position while the variable optical element 10 is rotated. Thus, a rotational position by which the wave front aberration for the entire optical unit 50 should be minimum can be obtained. Finally, the frame member 20 and the frame member 32 are fixed by a bonding agent at such a rotational position.

Here, in a case in which the frame member 20 and the frame member 32 are not fixed together, a mark 2 is disposed on such a rotational position on frame member 20 such that a part of the mark 2 is connected to a part of the mark 3. This is for a purpose of convenience so as to dispose the variable optical element 10 and the optical system 31 separately.

Such a third method for disposing the marks 2 and 3 is effective in a case in which the wave front aberration which is generated in the cover glasses 15 and 16 is fewer than the wave front aberration which is generated in the interface 12 and the optical system 31.

Here, it is quite often not to know which of the wave front aberration is the greatest or the fewest among the interface 12, the cover glasses 15 and 16, and the optical system 31. Therefore, it is preferable to obtain the fewest wave front aberration by performing the above methods.

Operational function by the marks 2 and 3 are explained in the image capturing device 40 having the above structure.

For example, it is assumed that an image of an object is captured by using the image capturing device 40. It is assumed that the object is positioned horizontally far away. In such a case, the image capturing device 40 is disposed such that the optical axis A of the optical unit 50 should be horizontal. In such a case, the image capturing device 40 is disposed such that the marks 2 and 3 should be disposed so as to coincide the highest position in the frame member 20 and the frame member 32 respectively with reference to the reference position. Alternatively, after the image capturing device 40 is disposed appropriately, the image capturing device 40 is rotated around the optical axis A until the marks 2 and 3 are disposed at the highest position in the frame member 20 and the frame member 32 respectively.

By disposing the image capturing device 40 in the above manner, it is possible to restrict the wave front aberration which is generated in the optical unit 50 in a minimum level. Therefore, it is possible to capture an image in which the wave front aberration is restricted in a minimum level.

Here, in the present embodiment, explanations are made for a case in which an optical system 31 is used. However, more importantly, it is acceptable if two or more optical systems 31 are used. In such a case, the optical systems 31 are assembled such that a relative rotation can be performed. Consequently, a rotational position at which the wave front aberration should be fewer than a predetermined value. Thus, it is acceptable if a mark is disposed at an appropriate position at such a rotational position. Here, an a method for attaching the variable optical element 10 and the optical system 31 is not limited to a bonding method. For example, it is possible to fix the variable optical element 10 and the optical system 31 by screws. Also, the image capturing element 41 is not limited to a CCD. For example, it is acceptable if the image capturing element 41 may be a Complementary Metal-Oxide Semiconductor (hereinafter called a CMOS).

Next, an image capturing device 42 according to a third embodiment of the present invention is explained with reference to FIG. 9. Here, it should be noted that, in explanations for the image capturing device 42, the same reference numerals are applied to corresponding members as shown in the above explanation for the variable optical element 10 so as to omit the repeated explanation thereof.

Figure 9:
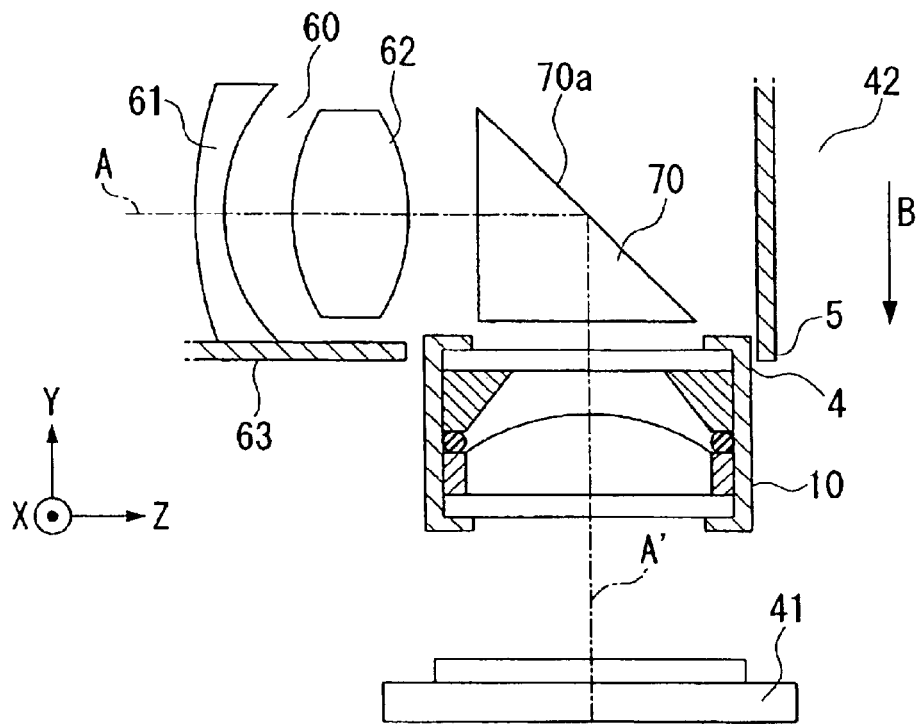
FIG. 9 is a cross section for an image capturing device according to a third embodiment of the present invention.

As shown in FIG. 9, the image capturing device 42 comprises an optical system 60, a prism (reflecting member) 70, a variable optical element 10 for condensing a light from the prism 70, and an image capturing element 41. Here, the prism 70 is used for deflecting a light which is emitted from the optical system 60. Also, the variable optical element 10 is used for condensing a light which is emitted from the prism 70. The image capturing element 41 is disposed at an image position which is formed by the optical system 60 and the variable optical element 10.

The optical system 60 comprises a concave lens 61 and a convex lens 62. Also, the optical system 60 is disposed such that the optical axis A of the optical system 60 should be horizontal.

The prism 70 serves for reflecting and deflecting a light. A light-incident surface and a light-emitting surface of the prism 70 are formed as a plane. A reflecting surface 70a of the prism 70 is disposed so as to be 45° in a Y-Z plane. Thus, the optical axis A is bent by 90° such that an optical axis A' is disposed vertical. In addition, the variable optical element 10 is disposed on the optical axis A'.

In the present embodiment, the variable optical element 10 is disposed on the vertical optical axis A'. In such a case, a gravity is applied on an entire interface 12. Therefore, a partial deformation does not occur on the interface 12 due to the gravity. However, very slight partial deformation may occur due to a manufacturing tolerance in the first ring electrode 17 and the ring seal member 19. As a result, a wave front aberration is generated on the interface 12. Therefore, a mark (index) 4 is disposed on an outer surface of the frame member 20 in the present embodiment.

Such a position of the mark 4 indicates that the wave front aberration is minimum in feasible combination of the optical system 60 and the prism 70.

It is explained below how the mark 4 serves in the image capturing device 42 having the above structure.

In the image capturing device 42, an optical system has an optical axes A and A' which are orthogonal to each other. Therefore, in the image capturing device 42, an entire optical system does not rotated around the optical axis. Such a feature is different from the above embodiments. Therefore, the mark 4 is used when the optical system in the image capturing device 42 is assembled.

In FIG. 9, the optical system 60 and the prism 70 are supported by a frame member 63. Thus, the frame member 63 is connected to the frame member 20 similarly to a case for the frame member 32 shown in FIG. 7. In such a case, the frame member 20 can rotate around the frame member 63. Therefore, the mark 5 (index) which is disposed on the frame member 63 and the mark 4 which is disposed on the frame member 20 are disposed so as to coincide with each other. After fixing the frame member 63 and the frame member 20, it is possible to assemble an optical system in which the wave front aberration is minimum.

Figure 10:
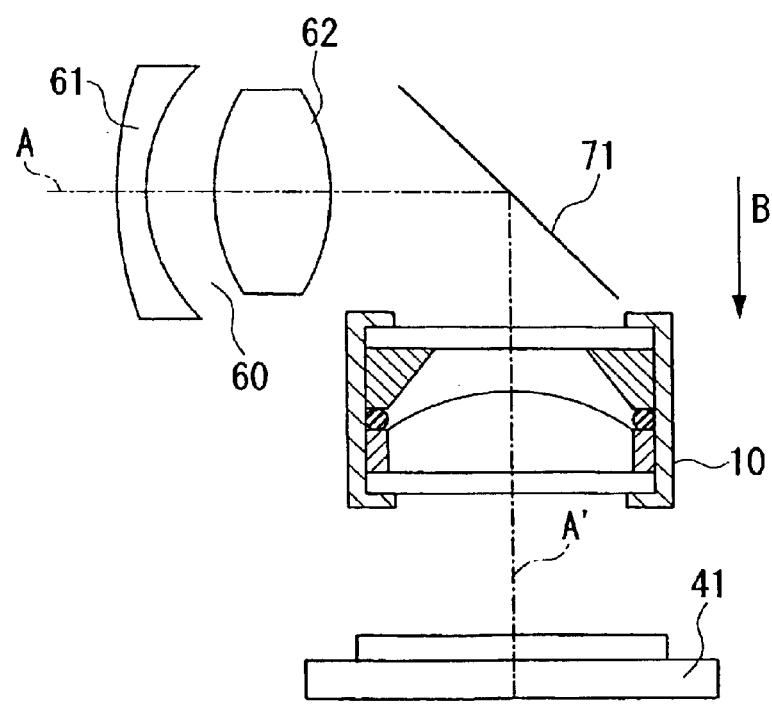
FIG. 10 is a modified example for an image capturing device shown in FIG. 9.

Here, in the present embodiment, it is acceptable if the light-incident surface and the light-emitting surface of the prism 70 may be refractive surfaces. As shown in FIG. 10, the prism 70 is used for a reflecting member. However, it is acceptable if a mirror 71 is used for a reflecting member. Here, it is preferable to restrict the wave front aberration to be 2λ or fewer which is generated in the optical system 60. If the image capturing element 41 which has more than a million pixels is used, it is preferable that the wave front aberration which is generated in the optical system 60 should be 1λ or fewer. Here, "λ" indicates a wavelength of a d-line. Here, it is necessary to obtain a sufficient back-forcus length in the optical system 60. Therefore, it is preferable that the optical system 60 should be a retro-focus optical system in which a concave lens having a negative power is disposed in front most of the optical system.

Next, examples for applying the present variable optical element to various devices are shown below. In FIG. 1, an example is shown in which the above image capturing device 42 is used for a mobile phone 43. In such a case, it is possible to vary the interface 12 in the variable optical element 10 according to a voltage which is applied to the first ring electrode 17 and the second ring electrode 18. By doing this, it is possible to realize an auto-focusing function and a zooming operation.

Figure 11A:
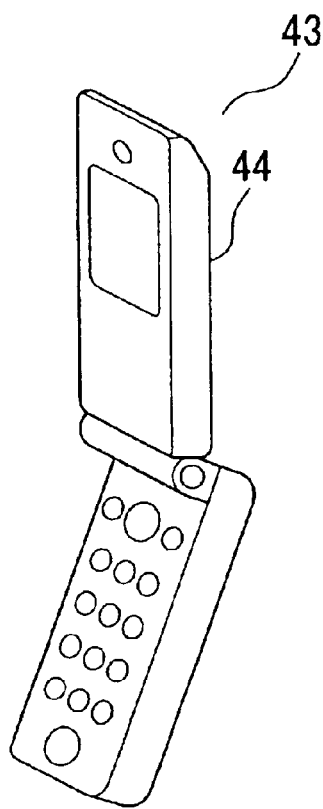
FIGS. 11A and 11B are examples in which the present invention is applied for a mobile phone.
Figure 11B:
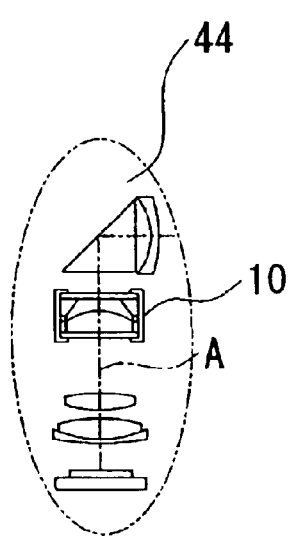

As shown in FIG. 11, under an ordinary condition for capturing an image of an object, the mobile phone 43 is used such that a longitudinal direction of a casing 44 is disposed vertically. Therefore, the optical axis A in the variable optical element 10 is disposed vertical. Therefore, by using the image capturing device 42 shown in FIGS. 9 and 10, it is possible to obtain an image in which the wave front aberration is restricted in a minimum level.

Figure 12A:
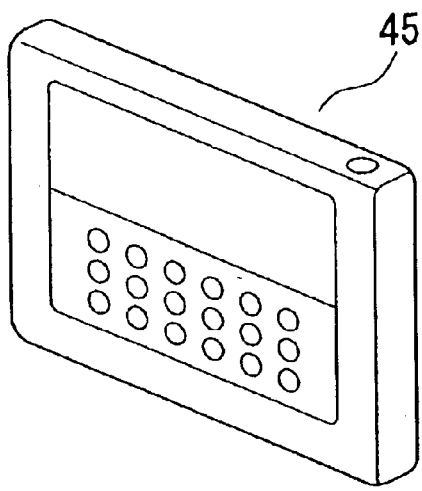
FIGS. 12A and 12B are examples in which the present invention is applied for a mobile terminal device.
Figure 12B:
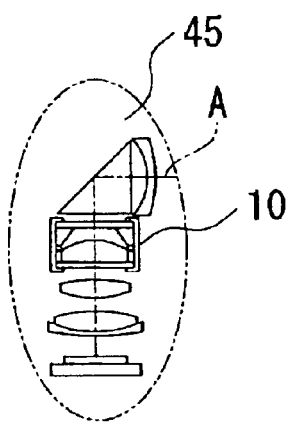

Here, as shown in FIG. 12, it is possible to use the image capturing device 42 in a mobile terminal device 45. The mobile terminal device 45 is an information inputting-outputting device such as a portable size personal computer. Alternatively, as shown in FIGS. 13A and 13B, it is possible to use the image capturing device 42 for a digital camera 46. Here, it is acceptable if the above variable optical element 10, an image capturing device in which the optical unit 30 is used, or an image capturing device 40 may be used in structures shown in FIGS. 11 and 12.

FIG. 14 shows an example for a structure for supplying an electricity to the image capturing device. Here, an electricity is supplied to the variable optical element 10 and the image capturing element 41 from a common power supply 48 via a controlling section 47. By doing this, it is possible to form a compact optical system for capturing an image. Here, it is possible to utilize such examples in the above mobile phone 43, the mobile terminal device 45, and above digital camera 46.

Figure 15:
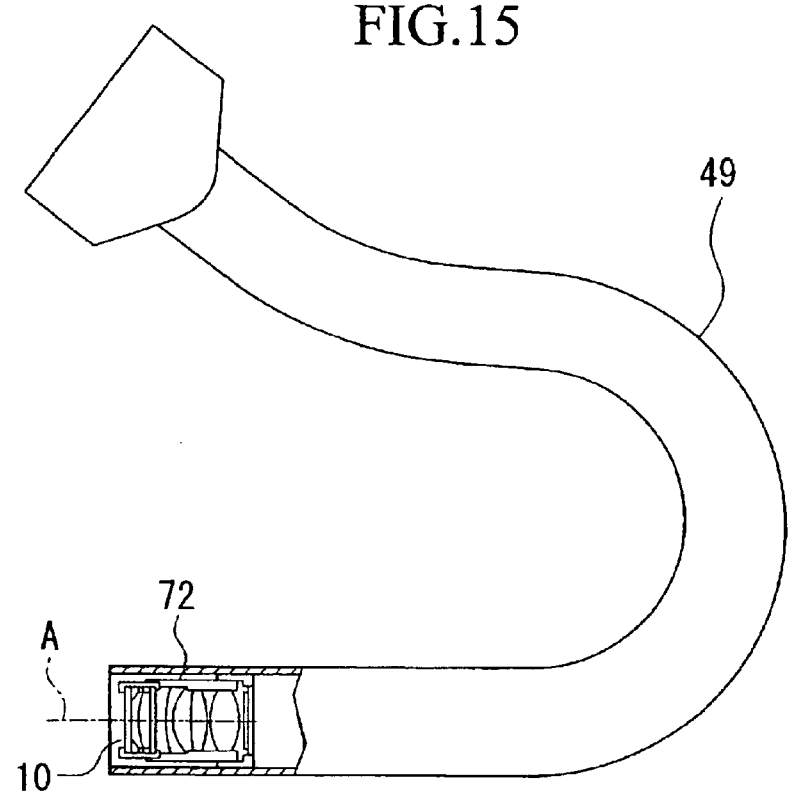
FIG. 15 shows an example in which the present invention is used in an endoscope.

Also, as shown in FIG. 15, it is possible to utilize the present variable optical element in an object optical system 72 in an endoscope 49. Here, the endoscope optical system 72 is disposed in the front most of the endoscope 49 so as to include the variable optical element 10. If a direction of the object optical system 2 can be designated desirably, it is possible to restrict the amount of the wave front aberration to be a predetermined amount or fewer by adjusting the rotational angle around the optical axis A such that the marks 2 and 3 should be disposed at predetermined positions.

Figure 16:
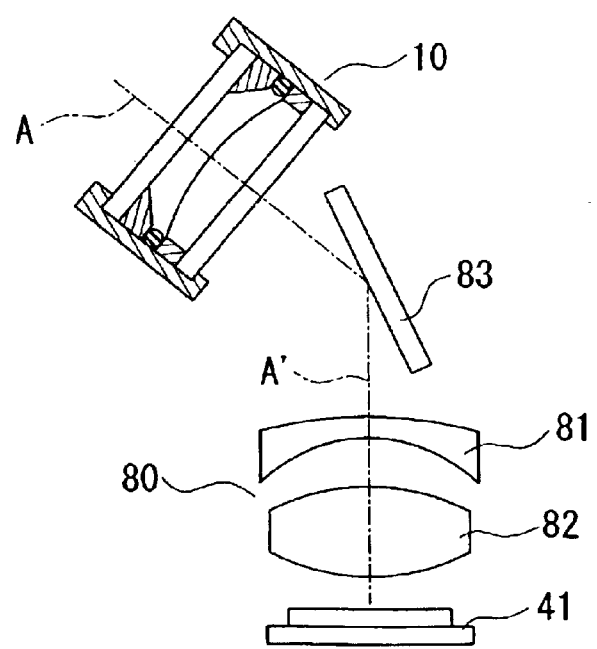
FIG. 16 is a modified example for an image capturing device.

Also, in the above embodiments, the optical axis A of the variable optical element 10 is disposed vertical or horizontal. However, it is not limited to such dispositions. For example, as shown in FIG. 16, it is possible to dispose the variable optical element 10 such that an inclination of the optical axis is disposed between the vertical direction and the horizontal direction. In FIG. 16, optical systems 80 and 83 which are formed by lenses 81 and 82 are mirrors.

Also, in the above embodiments, a central axis of the variable optical element 10 coincides with the optical axis. However, more importantly, it is acceptable if the central axis is disposed so as to be shifted or tilted with reference to the optical axis. It is understood that such a structure is employed for minimizing the wave front aberration in an entire optical system by the wave front aberration which is generated on the interface 12 intentionally.

According to the present embodiments, the rotational angle of the variable optical element around the optical axis is adjusted such that the index should be disposed at a predetermined position. Therefore, it is possible to restrict the wave front aberration to a predetermined level or fewer even if the optical axis is disposed approximately horizontally.

According to the present embodiments, the rotational angle of the optical unit around the optical axis is adjusted such that the index should be disposed at a predetermined position. Therefore, it is possible to restrict the wave front aberration in an entire optical unit to a predetermined level or fewer even if the optical axis is disposed approximately horizontally.

According to the present embodiments, the rotational angle of the optical unit around the optical axis is adjusted such that the variable optical element and the optical system are rotated relatively and the relative angle index should be disposed at a predetermined position. Therefore, it is possible further to reduce the wave front aberration in an entire optical unit even if the optical axis is disposed approximately horizontally.

According to the present embodiments, an optical axis in the variable optical element is approximately vertical. Also, an optical unit having a reflecting member is formed so as to have an optical axis which is orthogonal to the vertical direction. By doing this, it is possible to reduce the wave front aberration which is caused by an influence of the gravity.

According to the present embodiments, a variable optical element or an optical unit having a predetermined level or fewer wave front aberration is assembled in an image capturing device. By doing this, it is possible to capture an image in which the wave front aberration is restricted in a minimum level.

As explained above, the variable optical element and the optical unit are provided with a designating section and a relative angle designating section. Therefore, it is possible to restrict the wave front aberration to be a predetermined level or fewer which is caused by an influence of the gravity. Also, by using these variable optical element and optical unit in the image capturing device, it is possible to capture an image in which the wave front aberration is restricted in a minimum level.

What is claimed is:

1. A variable optical element comprising:
   a first liquid member;
   a second liquid member which is unsoluble in the first liquid member;
   a container which contains the first liquid member and the second liquid member;
   an index for positioning the variable optical element according to a predetermined reference,
   wherein an interfacial shape between the first liquid and the second liquid varies according to a voltage which is applied to the liquid members; and
   the index is disposed such that a wave front aberration in the variable optical element is minimum equal to or less than a predetermined value under condition that the variable optical element is positioned according to the predetermined reference.

2. A variable optical element according to claim 1 wherein:
   the predetermined reference is disposed horizontally; and
   an optical axis of the variable optical element is disposed so as to be parallel with the horizontal direction of the predetermined reference.

3. A variable optical element according to claim 1 wherein:
   the variable optical element and the optical element.

4. A variable optical element according to claim 1 further comprising a frame member for supporting the container wherein the index is disposed on the frame member.

5. A variable optical element according to claim 4 wherein shape of the frame member for supporting the container is rotationally asymmetrical around the optical axis.

6. A variable optical element according to claim 1 wherein the variable optical element is positioned according to the wave front aberration by measuring the surface of a transmitted wave.

7. A variable optical element according to claim 1 wherein a refractive index in the first liquid is different from a refractive index in the second liquid member.

8. An optical unit comprising:
   a variable optical element of claim 1; and
   at least an optical element,
   wherein the index is disposed such that a wave front aberration in the variable optical element should be minimum or fewer than a predetermined value under condition that the variable optical element is positioned according to the predetermined reference.

9. An optical unit according to claim 8 wherein:
   the predetermined reference is disposed horizontally; and
   an optical axis of the variable optical element is disposed so as to be parallel with the horizontal direction of the predetermined reference.

10. An optical unit according to claim 9 having an optical system which comprises:
    a variable optical element of which optical characteristics varies according to an interfacial shape between the first liquid and the second liquid according to a voltage which is applied to the liquid members; and
    at least a second optical element, wherein,
    the variable optical element and the second optical element can make a relative rotation around the optical axis,
    the index is formed by a fist index which is disposed on the variable optical element and a second index which is disposed on the second optical element, and
    the first index and the second index indicate a relative angle position made by the variable optical element around the optical axis which is used horizontally and the optical axis.

11. An optical unit according to claim 8 wherein the second optical element is a reflecting member.

12. An optical unit according to claim 11 wherein the variable optical element is disposed so as to be near the optical axis which is returned by the reflecting member.

13. An optical unit according to claim 12 wherein a central axis of the variable optical element is disposed so as to be approximately vertically parallel.

14. An optical unit according to claim 11 wherein the reflecting member is a mirror.

15. An optical unit according to claim 11 wherein the reflecting member is a prism.

16. An optical unit comprising:
a variable optical element of claim 1; and
at least a second optical element, and
two frame members for supporting the variable optical element and the second optical element, wherein
the indices are disposed in the frame members respectively.

17. An optical unit comprising:
a variable optical element of claim 1; and
an optical system which is provided with a first group having a negative refracting force and a second group having a positive refracting force.

18. An optical unit according to claim 17 wherein the optical system is disposed nearer the variable optical element than an object to be observed.

19. An image capturing device comprising:
a variable optical element of claim 1, or an optical unit of claim 8; and
an image capturing element.

20. An image capturing device according to claim 19 further comprising:
a driving unit for driving the variable optical element; and
a power supply unit for supplying an electricity to the image capturing element and the driving unit.

21. A mobile phone comprising:
a variable optical element of claim 1;
a displaying section;
an inputting button section;
a voice inputting-outputting section; and
an antenna.

22. A digital camera comprising:
a variable optical element of claim 1:
a displaying section; and
an operating section.

23. An endoscope device comprising:
a variable optical element of claim 1:
a light source;
a signal processing circuit; and
a power supply section.

24. Mobile terminal comprising:
a variable optical element of claim 1:
a displaying section; and
a key board.

25. A variable optical element comprising:
a first liquid member;
a second liquid member which is insoluble in the first liquid member;
a container which contains the first liquid member and the second liquid member;
an index for positioning the variable optical element according to a predetermined reference,
wherein an interfacial shape between the first liquid and the second liquid varies according to a voltage which is applied to the liquid members; and
the index is disposed such that a wave front aberration in the variable optical element is a minimum under the condition that the variable optical element is positioned according to the predetermined reference.

* * * * *

UNITED STATES PATENT AND TRADEMARK OFFICE
CERTIFICATE OF CORRECTION

PATENT NO. : 6,934,090 B2
APPLICATION NO. : 10/822132
DATED : August 23, 2005
INVENTOR(S) : Toshlyuki Nagaoka and Tetsuhide Takeyama It is certified that error appears in the above-identified patent and that said Letters Patent is hereby corrected as shown below:

Column 57, line 2 "unsoluble" with -- Insoluble --
Column 3, line 48, replace "fist" with -- first --
Column 12, line 27, replace "forcus" with -- focus --
Column 13, line 64, replaced "unsoluble" with -- insoluble --
Column 14, line 67, replace "fist" with -- first --.

Signed and Sealed this

Twenty-second Day of August, 2006

JON W. DUDAS
*Director of the United States Patent and Trademark Office*